(12) United States Patent
Weinert et al.

(10) Patent No.: US 9,092,553 B2
(45) Date of Patent: *Jul. 28, 2015

(54) METHOD AND SYSTEM FOR CALCULATING DAILY WEIGHTED AVERAGES OF GLUCOSE MEASUREMENTS (OR DERIVED QUANTITIES) WITH TIME BASED-WEIGHTS

(75) Inventors: Stefan Weinert, Pendleton, IN (US); Ajay Thukral, Indianapolis, IN (US)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 570 days.

This patent is subject to a terminal disclaimer.

(21) Appl. No.: 13/439,935

(22) Filed: Apr. 5, 2012

(65) Prior Publication Data

US 2012/0197536 A1   Aug. 2, 2012

Related U.S. Application Data

(63) Continuation of application No. 12/215,175, filed on Jun. 25, 2008, now Pat. No. 8,175,812.

(51) Int. Cl.
  *C12Q 1/00* (2006.01)
  *G06F 19/00* (2011.01)
  *A61B 5/145* (2006.01)

(52) U.S. Cl.
  CPC ........ *G06F 19/3406* (2013.01); *A61B 5/14532* (2013.01); *C12Q 1/00* (2013.01); *G06F 19/3456* (2013.01)

(58) Field of Classification Search
  CPC .......................................................... C12Q 1/00
  USPC .............................................................. 435/4
  See application file for complete search history.

(56) References Cited

U.S. PATENT DOCUMENTS

| 4,151,845 | A | 5/1979 | Clemens |
| 5,720,733 | A * | 2/1998 | Brown .......................... 604/207 |
| 6,326,160 | B1 | 12/2001 | Dunn et al. |
| 6,424,847 | B1 | 7/2002 | Mastrototaro et al. |
| 6,954,662 | B2 | 10/2005 | Freger et al. |
| 8,175,812 | B2 * | 5/2012 | Weinert et al. .................. 702/19 |
| 2002/0126036 | A1 * | 9/2002 | Flaherty et al. ............... 341/176 |
| 2004/0059201 | A1 | 3/2004 | Ginsberg |
| 2007/0010950 | A1 | 1/2007 | Abensour et al. |

FOREIGN PATENT DOCUMENTS

| WO | 01/13786 A1 | 3/2001 |
| WO | 2007081853 A2 | 7/2007 |

* cited by examiner

*Primary Examiner* — Ardin Marschel
(74) *Attorney, Agent, or Firm* — Harness, Dickey

(57) ABSTRACT

A method and system for calculating daily weighted averages of glucose measurements (or derived quantities) with time-based weights are disclosed. The present invention computes an average daily glucose value using the time based weights based on only consecutive glucose measurements in the plurality of glucose measurements with acceptable time intervals that do not exceed a predefined maximum time interval. The invention further relates to a computer program for implementing the method for calculating daily weighted averages of spot monitoring glucose measurements (or derived quantities) with the time-based weights.

9 Claims, 9 Drawing Sheets

METHOD AND SYSTEM FOR CALCULATING DAILY WEIGHTED AVERAGES OF GLUCOSE MEASUREMENTS (OR DERIVED QUANTITIES) WITH TIME BASED-WEIGHTS

CROSS REFERENCE TO RELATED APPLICATIONS

This application is a continuation of U.S. patent application Ser. No. 12/215,175, filed Jun. 25, 2008.

FIELD OF THE INVENTION

Embodiments of invention relate to physiological monitoring, and in particular to a method and system for calculating daily weighted averages of glucose measurements (or derived quantities) with time-based weights. Embodiments of invention further relate to a computer program for implementing the method for calculating daily weighted averages of glucose measurements (or derived quantities) with time-based weights.

BACKGROUND OF THE INVENTION

Monitoring parameters measured in or on the body of humans such as a concentration of a certain substance in a given body fluid has many applications. In particular, the monitoring is crucial in the context of therapies that involve an administration of active substances regulated depending on the value of one or a plurality of physiological parameters. A prominent example is diabetes therapy where the administration of insulin is effected depending on a measured glucose concentration in a body fluid of the patient.

Conventionally, diabetic patients who need to regularly administer insulin have periodically taken measurements (usually four a day) of their glucose level, e.g. using a spot monitoring device such as, for example, a hand held strip-based glucose meter. However, patients measuring their glucose concentration with a spot monitoring device several times per day may temporarily increase their measuring frequency after encountering hypo- or hyperglycemic events to check if they move out of this undesirable condition. This can be done with or without an intervention like ingesting fast acting carbohydrates or taking glucose lowering measures. Such a temporary increase of the measurement frequency will skew the result of any direct arithmetic averaging process applied to the glucose data since the same basic event in time (e.g. the hypoglycemia) is represented by several additional measurements.

SUMMARY OF THE INVENTION

It is against the above background that the present invention provides a method, system, and computer program product for calculating daily weighted averages of glucose measurements (or derived quantities) with time-based weights. Applying the time-based weighting scheme according to the present invention to spot glucose measurements reduces the impact of an event-triggered change in self-monitored, glucose measurement frequency.

In one embodiment, a method for calculating daily weighted averages of glucose measurements with time-based weights is disclosed. The method comprises providing a plurality of glucose measurements each collected at a different time, and determining whether each time interval between two consecutive glucose measurements in the plurality of glucose measurements exceeds a predefined maximum time interval length. The method further includes computing electronically an average daily glucose value, which represents the daily weighted average of the glucose measurements, using time based weights based on only consecutive glucose measurements in the plurality of glucose measurements with acceptable time intervals that do not exceed the predefined maximum time interval, and providing the computed daily weighted average of the glucose measurements.

In another embodiment, a system for calculating daily weighted averages of glucose measurements with time-based weights is disclosed. The system comprises a processor programmed to: receive a plurality of glucose measurements each collected at a different period of time; determine whether each time interval between two consecutive glucose measurements in the plurality of glucose measurements exceeds a predefined maximum time interval value; compute an average daily glucose value, which represents the daily weighted average of the glucose measurements, using time based weights based on only consecutive glucose measurements in the plurality of glucose measurements with acceptable time intervals that do not exceed the predefined maximum time interval; and provide the computed daily weighted average of the glucose measurements.

In still another embodiment, a computer program product is disclosed which comprises code that when executed by a processor based system performs the method steps of present invention disclosed herein.

These and other advantages and features of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which.

DETAILED DESCRIPTION

The present invention may be implemented using hardware, software or a combination thereof and may be implemented in one or more microprocessor based systems, such as a portable computer or other processing systems, such as personal digital assistants (PDAs), or directly in self-monitoring glucose devices or meters (bG meters) equipped with adequate memory and processing capabilities to process a chronological sequence of measurements of a time dependent parameter measured in or on the human body, namely of the glucose level (e.g. the glucose (bG) level).

Figure 1:
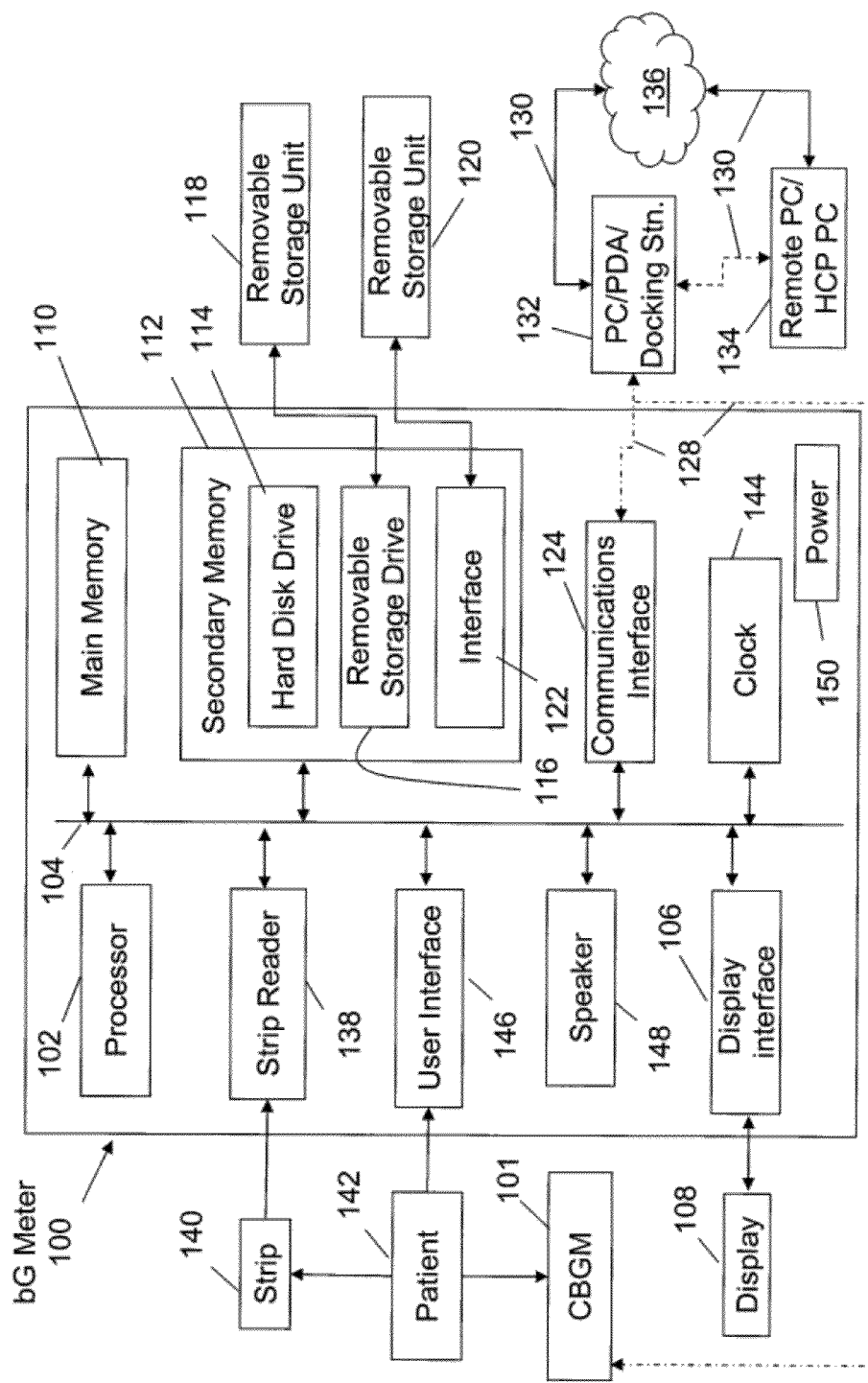
FIG. 1 is a block diagram of one embodiment of a processor based system for implementation of the present invention.

In an example embodiment, the present invention is implemented in software running on a self-monitoring blood glucose (bG) meter 100 as illustrated in FIG. 1. The bG meter 100 is common in the industry and includes essentially any device that can function as a glucose acquisition mechanism. The bG meter 100 or acquisition mechanism, device, tool, or system includes various conventional methods directed toward drawing a sample (e.g. by finger prick) for each test, and making a spot determination of the glucose level using an instrument that reads glucose concentrations by optical, electrochemical, electromechanical or calorimetric detection/measurement methods. In addition, the bG meter 100 may include indwelling catheters and subcutaneous tissue fluid sampling devices and/or communicate with devices, such as continuous glucose monitor (CGM) 101, having indwelling catheters and subcutaneous tissue fluid sampling devices.

In the illustrated embodiment, the bG meter 100 includes one or more microprocessors, such as processor 102, which is connected to a communication bus 104, which may include data, memory, and/or address buses. The bG meter 100 may include a display interface 106 providing graphics, text, and other data from the bus 104 (or from a frame buffer not shown) for display on a display 108. The display interface 106 may be a display driver of an integrated graphics solution that utilizes a portion of main memory 110 of the meter 100, such as random access memory (RAM) and processing from the processor 102 or may be a dedicated graphics card. In another embodiment, the display interface 106 and display 108 additionally provide a touch screen interface for providing data to the bG meter 100 in a well known manner.

Main memory 110 in one embodiment is random access memory (RAM), and in other embodiments may include other memory such as a ROM, PROM, EPROM or EEPROM, and combinations thereof. In one embodiment, the bG meter 100 includes secondary memory 112 which may include, for example, a hard disk drive 114 and/or a removable storage drive 116, representing a floppy disk drive, a magnetic tape drive, an optical disk drive, a flash memory, etc. The removable storage drive 116 reads from and/or writes to a removable storage unit 118 in a well known manner. Removable storage unit 118, represents a floppy disk, magnetic tape, optical disk, etc. which is read by and written to by removable storage drive 116. As will be appreciated, the removable storage unit 118 includes a computer usable storage medium having stored therein computer software and/or data.

In alternative embodiments, secondary memory 112 may include other means for allowing computer programs or other instructions to be loaded into the bG meter 100. Such means may include, for example, a removable storage unit 120 and an interface 122. Examples of such removable storage units/ interfaces include a program cartridge and cartridge interface, a removable memory chip (such as a ROM, PROM, EPROM or EEPROM) and associated socket, and other removable storage units 120 and interfaces 122 which allow software and data to be transferred from the removable storage unit 120 to the bG meter 100.

The bG meter 100 in one embodiment includes a communications interface 124. The communications interface 124 allows software and data to be transferred between the bG meter 100 and an external device(s) 126. Examples of communications interface 124 may include one or more of a modem, a network interface (such as an Ethernet card), a communications port (e.g., USB, firewire, serial or parallel, etc.), a PCMCIA slot and card, a wireless transceiver, and combinations thereof. In one embodiment, the external device 126 is a personal computer (PC), and in another embodiment is a personal digital assistance (PDA). In still another embodiment, the external device 126 is a docking station wherein the communication interface 124 is a docket station interface. In such an embodiment, the docking station 126 may provided and/or connect to one or more of a modem, a network interface (such as an Ethernet card), a communications port (e.g., USB, firewire, serial or parallel, etc.), a PCMCIA slot and card, a wireless transceiver, and combinations thereof. Software and data transferred via communications interface 124 are in the form of wired or wireless signals 128 which may be electronic, electromagnetic, optical, or other signals capable of being sent and received by communications interface 124. For example, as is known, signals 128 may be sent between communication interface 124 and the external device(s) 126 using wire or cable, fiber optics, a phone line, a cellular phone link, an RF link, an infrared link, other communications channels, and combinations thereof.

In one embodiment, the external device 126 is used for establishing a communication link 130 between the bG meter 100 and still further electronic devices such as a remote Personal Computer (PC) of the patient, and/or a health care provider (HCP) computer 134, directly or indirectly, such as through a communication network 136, such as the Internet and/or other communication networks. The communication interface 124 and/or external device(s) 126 may also be used to communicate with further data gathering and/or storage devices such as insulin delivering devices, cellular phones, personal digital assistants (PDA), etc. Specific techniques for connecting electronic devices through wired and/or wireless connections (e.g. USB and Bluetooth, respectively) are well known in the art.

In the illustrative embodiment, the bG meter 100 provides a strip reader 138 for receiving a glucose test strip 140. The test strip 140 is for receiving a sample from a patient 142, which is read by the strip reader 138. Data, representing the information provided by the test strip, is provided by the strip reader 138 to the processor 102 which executes a computer program stored in memory 110 to perform various calculations as discussed in great detail below on the data. The results of the processor 102 from using the data is displayed on the display 108 and/or recorded in secondary memory 110, which is herein referred to as self monitored glucose (bG) data. The bG data may include, but not limited thereto, the glucose values of the patient 142, the insulin dose values, the insulin types, and the parameter values used by processor 102 to calculate future glucose values, supplemental insulin doses, and carbohydrate supplements. Each glucose value and insulin dose value is stored in memory 112 with a corresponding date and time. An included clock 144 of the bG meter 100 supplies the current date and time to processor 102.

The bG meter 100 further provides a user input device(s) 146 such as keys, touchpad, touch screen, etc. for data entry, program control, information requests, and the likes. A speaker 148 is also connected to processor 102, and operates under the control of processor 102 to emit audible alerts/reminders to the patient, such as for example, to take a meal, of possible future hypoglycemia, and the likes. A suitable power supply 150 is also provided to power the bG meter 100 as is well known to make the meter portable.

The terms "computer program medium" and "computer usable medium" are used to generally refer to media such as removable storage drive 116, a hard disk installed in hard disk drive 114, signals 128, etc. These computer program products are means for providing software to bG meter 100. The invention includes such computer program products.

Computer programs (also called computer control logic) are stored in main memory 110 and/or secondary memory 112. Computer programs may also be received via the communications interface 124. Such computer programs, when executed, enable the bG meter 100 to perform the features of the present invention as discussed herein. In particular, the computer programs, when executed, enable processor 102 to perform the functions of the present invention. Accordingly, such computer programs represent controllers of bG meter 100.

In an embodiment where the invention is implemented using software, the software may be stored in a computer program product and loaded into bG meter 100 using removable storage drive 116, removable storage unit 120, hard drive 114, or communications interface 124. The control logic (software), when executed by the processor 102, causes the processor 102 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described hereafter are implemented in the C++ programming language, but could be implemented in other programs such as, but not limited to, Visual Basic, C, C#, Java or other programs available to those skilled in the art.

As mentioned above, the bG meter 100 is used by the patient 142 for recording, inter alia, insulin dosage readings and spot measured glucose levels. Such bG data obtained by the bG meter 100 in one embodiment is transferable via the communication interface 124 to another electronic device, such the external device 126 (PC, PDA, or cellular telephone), or via the network 136 to the remote PC and/or HCP computer 134. Examples of such bG meters include but are not limited to, the Accu-Chek Active meter and the Accu-Chek Aviva system both by Roche Diagnostics, Inc. which are compatible with the Accu-Chek 360° Diabetes management software to download test results to a personal computer or the Accu-Chek Pocket Compass Software for downloading and communication with a PDA.

Accordingly, it is to be appreciated that the bG meter 100 includes the software and hardware necessary to process, analyze and interpret the self-recorded diabetes patient (i.e., bG) data in accordance with predefined flow sequences (as described below in detail) and generate an appropriate data interpretation output. In one embodiment, the results of the data analysis and interpretation performed upon the stored patient data by the bG meter 100 are displayed in the form of a report, trend-monitoring graphs, and charts to help patients manage their physiological condition and support patient-doctor communications. In other embodiments, the bG data from the bG meter 100 may be used to generated reports (hardcopy or electronic) via the external device 126 and/or personal computer (PC) and/or HCP computer 134.

The bG meter 100 further provides the user and/or his or her HCP with the possibilities of a) editing data descriptions, e.g. the title and description of a record; b) saving records at a specified location, in particular in user-definable directories as described above; c) recalling records for display; d) searching records according to different criteria (date, time, title, description etc.); e) sorting records according to different criteria (values of the bG level, date, time, duration, title, description etc.); f) deleting records; g) exporting records; and/or h) performing data comparisons as is well known.

It is to be appreciated that the present invention enhances existing software and/or hardware that retrieves and processes the bG data. The methods and system of the invention can be directly incorporated into existing home glucose monitors, or used for the enhancement of software that retrieves and processes bG data, by introducing a process for calculating daily weighted averages of spot monitoring glucose measurements (or derived quantities) with time-based weights.

One aspect of the invention includes a method, system, and computer program product for calculating a time-weighted average of bG results (i.e., bG data) collected over a predetermined period, for example 4-6 weeks.

The following gives a general description of the approach for calculating a time-weighted average of bG results for a given day. For example, some people measure their sugar regularly several times per days; other will vary their measurement frequency considerably; in extreme cases there will be periods of time (e.g. several days) where no measurements are taken at all. The logic that underlies the method must be able to handle these cases in order to be implemented on the bG meter 100.

Figure 2:
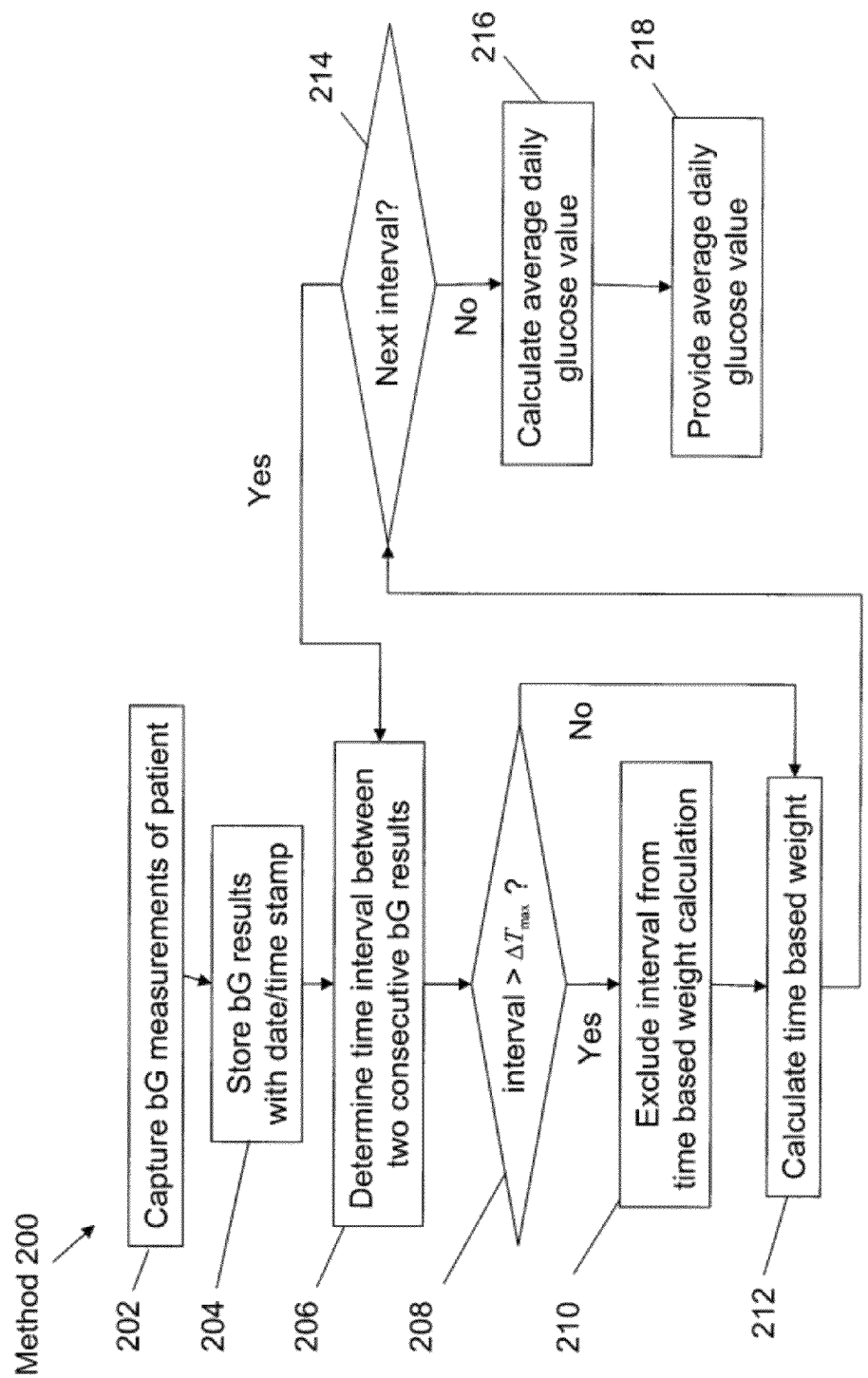
FIG. 2 is a flow diagram of one embodiment of a method for implementation of the present invention.

With reference to FIG. 2, the method 200 of the present invention is described. In step 202, bG (i.e., spot) measurements of the patient 142 is captured. In one embodiment, each of the bG measurements is captured via strip 140 provided with a sample of the patient's which is then in turn read by strip reader and analyzed by processor 102 to give the bG measurement of the patient 142. In other embodiments, the bG measurements may be captured at times dictated by the continuous glucose monitor 101 and/or commanded by the patient. As is well know the result of a newly taken bG measurements is displayed to the patient on display 108 as well as stored such as, for example, in memory 112 together with a time and date of the measurement, via processor 102 reading clock 148 in step 204. An example of such bG results is graphically depicted by FIG. 3 to which reference is also made.

Figure 3:
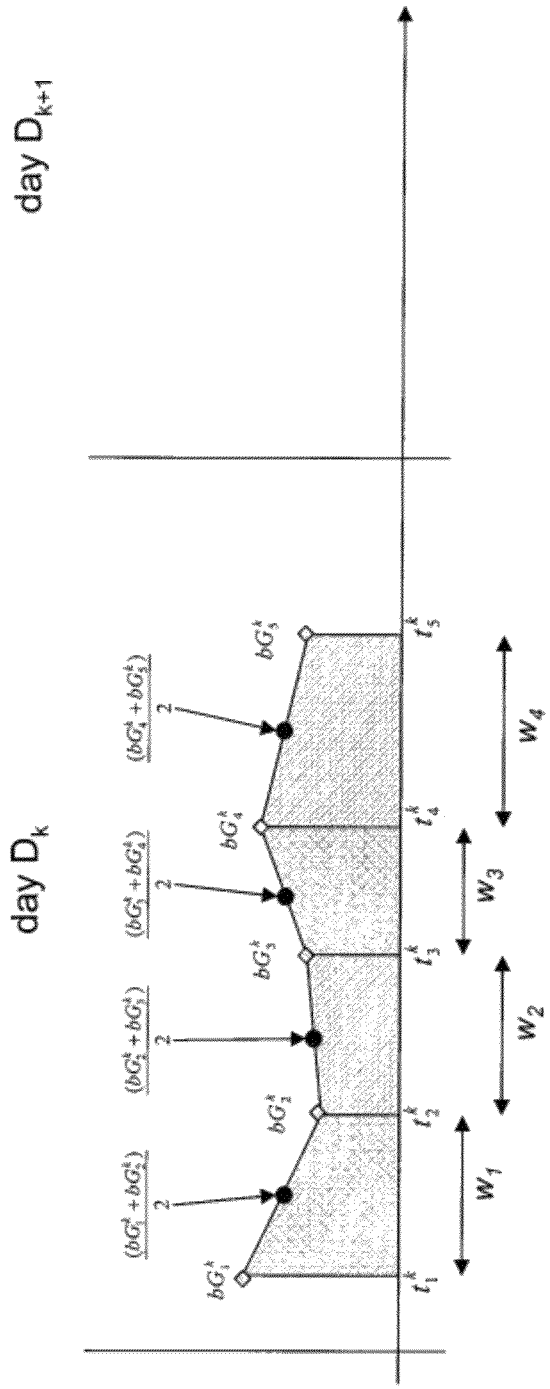
FIG. 3 is a graphical representations of calculating daily weighted averages of spot monitoring glucose measurements (or derived quantities) with time-based weights according to the present invention.

As shown by FIG. 3, in one embodiment and generally, as mentioned above the bG meter 100 stores the results of the glucose (bG) measurements in its memory 112 together with a date and time stamp to create a chronological sequence or set G of bG spot measurements, such as measurements $bG_1^k$, $bG_2^k$, $bG_3^k$, $bG_4^k$, and $bG_5^k$, where k is the day. The measurement set G is sorted by increasing time and may span several days. In one embodiment, the date stored in memory with the measurement consists of some representation of day/month/year, and the time consists of some representation of the time of day (e.g. hh:mm:ss). In other embodiments, other date and time recording methods may be used, such as for example, using a Julian calendar and an alternative count interval for time.

Generally, if two or more bG results exist in memory 112 for a given day Dk, then the method of the invention proceeds to check the time interval between consecutive bG results. In one embodiment, the bG meter 100 will assume that for each interval between two consecutive bG results whose length does not exceed a predefined maximum time interval value $\Delta T_{max}$ the glucose value for this interval can be reasonably approximated by the arithmetic average of the two bG results. The $\Delta T_{max}$ value is used in a weighting algorithm to limit the weight for a given measurement in case that the time interval between two consecutive measurements is too long to be acceptable. The present invention assumes that if the time interval is too long, then the behavior of the glucose in this interval is considered unknown. Thus, in step 206 (FIG. 2), the interval between two consecutive bG results such as, for example, the new bG result and the previous bG result, is determined by the processor 102.

In step 208, the result from step 206 is checked to see if the length of the interval between the two consecutive bG results exceeds $\Delta T_{max}$. If the length of the time interval between two consecutive bG results exceeds $\Delta T_{max}$, then the bG meter 100 in step 210 will exclude this interval from the daily weighted average bG calculation. In one embodiment, the weight associated with the time interval between the consecutive bG results is set to zero such that their average bG value will also receive a weight of zero. In other embodiment, other exclusion methods may be used, such as for example, flagging in memory 112 this interval to indicate it's exclusion if processing of the arithmetic averaging is performed at a later time.

After step 210, the bG meter 100 in step 212 then uses the consecutive bG measurements having acceptable intervals to calculate a set weighted sums sum_bG$_k$*, one for each day. Each of the weighted sums sum_bG$_k$* is the sum of the averages of consecutive bG measurements bG$_n$, bG$_{n+1}$ multiplied by the time interval $w_n$ between measurements.

In step 214 the bG meter 100 then checks for any additional measurement intervals in which to repeat steps 206-212 for all remaining intervals. Afterwards and next in step 216, the bG meter 100 computes a daily weight average avg_bG$_k$ by dividing the time based weighted sum_bG$_k$* by the sum of the time-based weights that were used in calculating the weighted sum sum_bG$_k$*. The next day is represented by day D$_{k+1}$ for which no measurements have been yet recorded. The formulae used in calculating the weighted sum for any given day D$_k$ is shown by Table 1.

TABLE 1

Formula for calculating weighted sum sum_bG$_k$* for any given day D$_k$

Let (bG$_n^k$, t$_n^k$), n = 1 to N$_k$, the bG results (with the corresponding times in minutes) of the k-th day with N$_k \geq 2$;

$$\text{sum\_bG}_k^* = \sum_{n=1}^{N_k-1} w_n \cdot \frac{bG_n + bG_{n+1}}{2}$$

with:

$$w_n = \begin{cases} t_{n+1}^k - t_n^k & \text{for } t_{n+1}^k - t_n^k \leq \Delta T_{max} \\ 0 & \text{else} \end{cases}$$

If N$_k$ < 2 then sum_bG$_k$* = 0.

It is to be appreciated that the average daily glucose value for any given day D$_k$ is calculated in step 216 when a next glucose measurement has been taken that is assigned a date later than a previous glucose measurement. The daily weighted average glucose value is then provided to the patient in step 218, such as for example, on display 108, and if desired, stored in memory 112 for later recall.

With reference now made to FIGS. 4-8, use cases are provided hereafter that further describe the pragmatic handling of situations by the method of the present invention that will exist when a person uses the bG meter 100 in real life.

Case 1

Figure 4A:
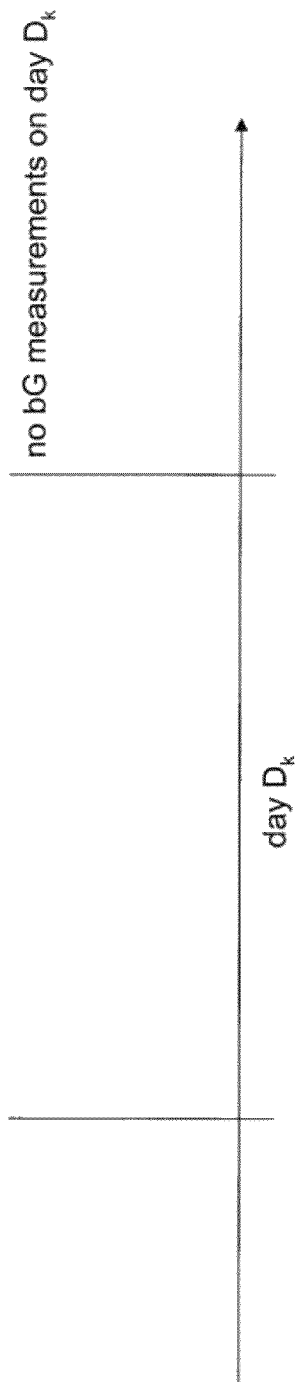
FIGS. 4a, 4b, and 4c are graphical representations of calculating daily weighted averages of spot monitoring glucose measurements (or derived quantities) with time-based weights in a first use case scenario according to the present invention.
Figure 4B:
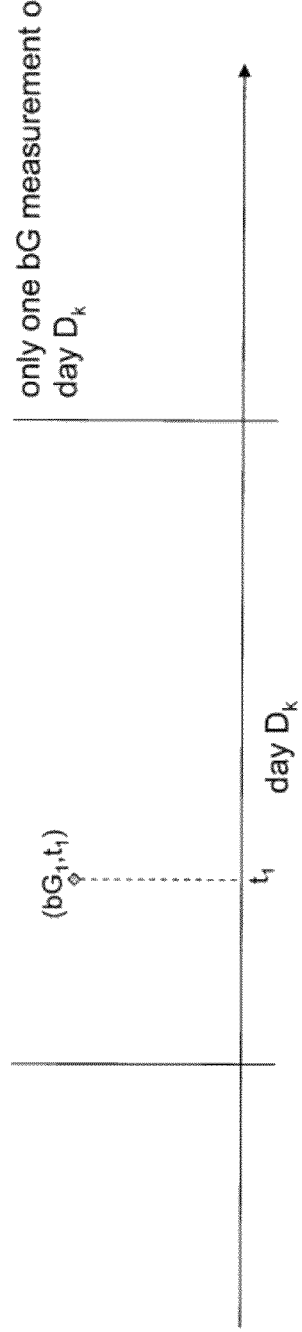
Figure 4C:
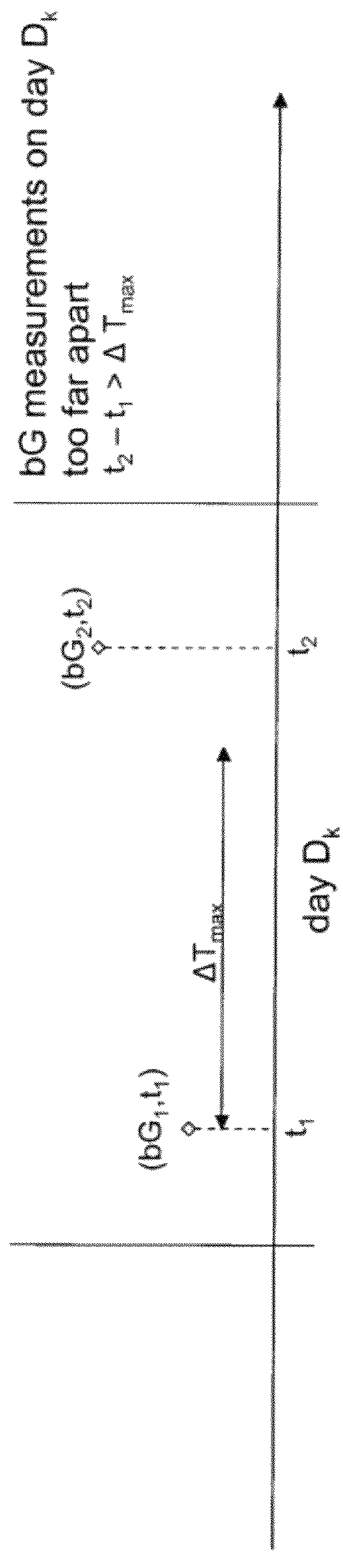

If the weighted sum sum_bG$_k$* for the given day D$_k$ is zero, then the weighted average glucose value, avg_bG$_k$ for the day D$_k$ will be set to not-a-number (NAN or NaN). It is to be appreciated that a result of NaN denotes that avg_bG$_k$ cannot be assigned a usable value. Such a result can occur when there is no or only one bG measurement provided during the day Dk, as shown by FIGS. 4a and 4b, respectively. This result may also occur even if two bG measurements were recorded for day Dk, but the consecutive bG measurements were too far apart thus exceeding the maximum time interval limit $\Delta T_{max}$ to be useful. This latter result is depicted by FIG. 4c.

Case 2

Figure 5A:
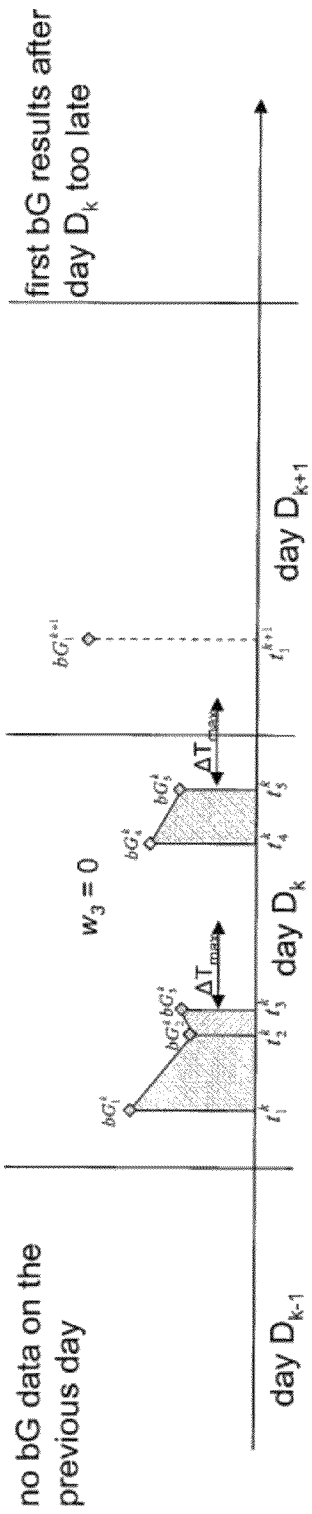
FIGS. 5a and 5b are graphical representations of calculating daily weighted averages of spot monitoring glucose measurements (or derived quantities) with time-based weights in a second use case scenario according to the present invention.
Figure 5B:
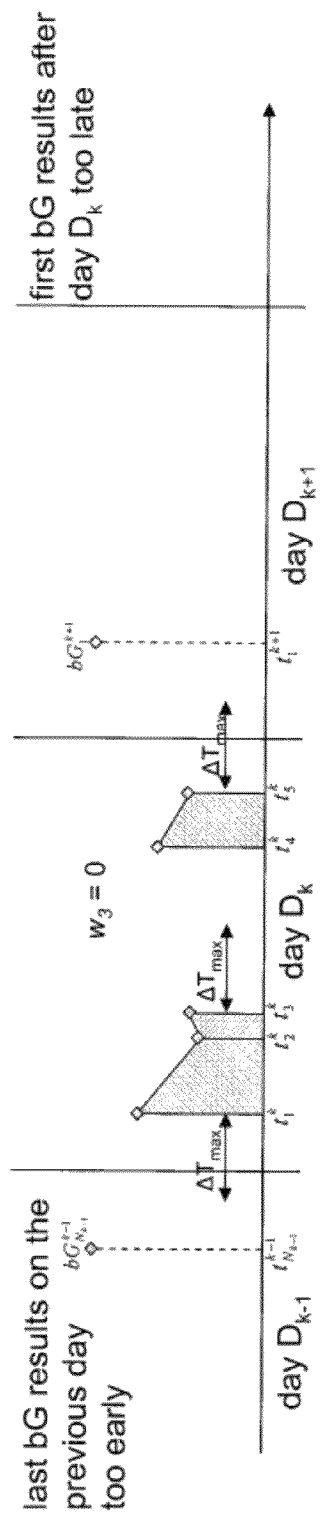

With reference to FIGS. 5a and 5b, in the second use case more than one bG measurements have been provided in the day D$_k$ which do not exceed the maximum time interval limit $\Delta T_{max}$. As shown by FIG. 5a, however, the time interval between spot measurements bG$_3^k$ and bG$_4^k$, and bG$_5^k$ and bG$_1^{k+1}$, which is taken the day after D$_{k+1}$, exceed the maximum time interval limit $\Delta T_{max}$, and therefore those two intervals are excluded from the averaging process. In one embodiment, the interval is excluded by setting the value of the corresponding interval weight to zero (e.g., w$_3$=0). As shown by FIG. 5b, from the previous day spot measurement bG$_{N_{k-1}}^{k-1}$, the maximum time interval limit $\Delta T_{max}$ to the first spot measurement on the next day D$_k$ is exceeded so that time interval would in that case also be excluded from the averaging process. Therefore, in such a use case situation, the following logic is employed by the method. If the average daily glucose value will not give a not_a_number result, avg_bG$_k \neq$NaN, and the day D$_k$ is the first day that the bG meter 100 has been used to collect glucose measurements or there are no results for the previous day D$_{k-1}$ or the last bG result of the previous day is more than the value $\Delta T_{max}$ before the first measurement of day D$_k$ and the first measurement after day D$_k$ is more than the value $\Delta T_{max}$ later than the last measurement on day D$_k$, then the average daily glucose value avg_bG$_k$ for day D$_k$ is calculated according to equation 1 hereafter.

$$\text{avg\_bG}_k = \frac{\text{sum\_bG}_k^*}{\sum_{n=1}^{N_k-1} w_n}. \tag{1}$$

Case 3

Figure 6:
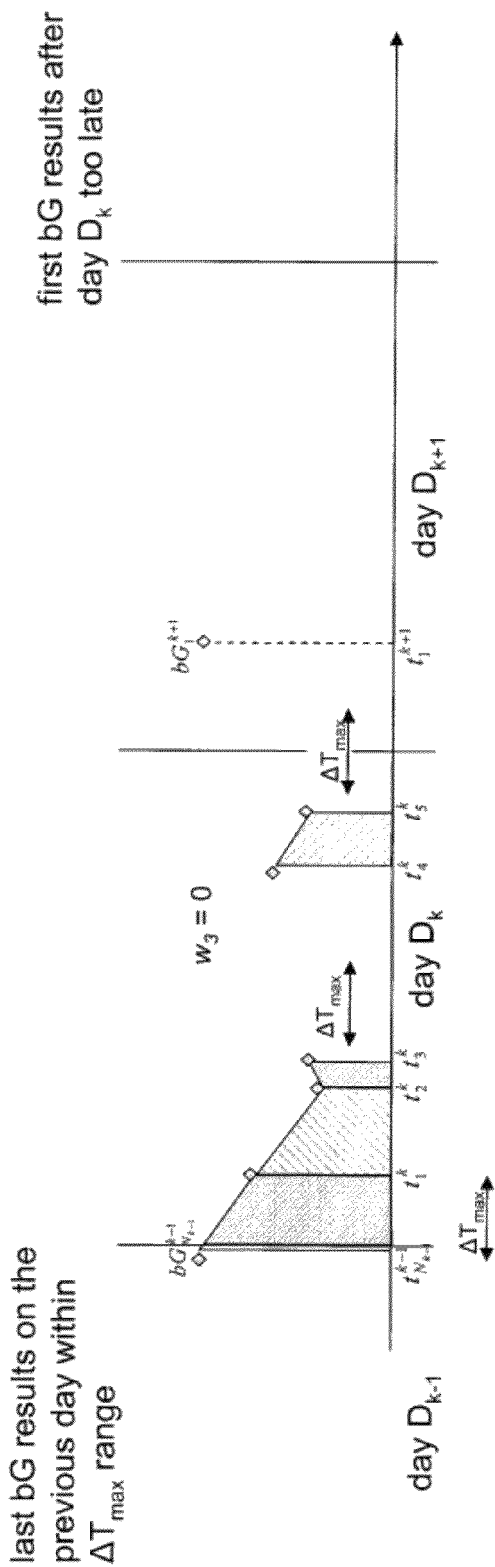
FIG. 6 is graphical representations of calculating daily weighted averages of spot monitoring glucose measurements (or derived quantities) with time-based weights in a third use case scenario according to the present invention.

With reference to FIG. 6, as shown the last bG result bG$_{N_{k-1}}^{k-1}$ on the previous day D$_{k-1}$ is within the maximum time interval value $\Delta T_{max}$; however, the first bG result bG$_1^{k+1}$ on the day after D$_k$ is too late, and the interval again between bG results bG$_3^k$ and bG$_4^k$ exceed the maximum time interval limit $\Delta T_{max}$. Therefore, in such a use case situation, the following logic is employed by the method. If the average daily glucose value will not give a not_a_number result, avg_bG$_k \neq$NaN, and the last bG result (bG$_{N_{k-1}}^{k-1}$t$_{N_{k-1}}^{k-1}$) of the previous day D$_{k-1}$ is less than or equal to $\Delta T_{max}$ before the first measurement of day D$_k$, and the first measurement after day D$_k$ is more than $\Delta T_{max}$ later than the last measurement on day $D_k$, then the average daily glucose value for $D_k$ is calculated according to equation (2) hereafter.

$$\text{avg\_bG}_k = \frac{\left(\text{sum\_bG}_k^* + t_1^k \cdot \left(bG_{N_{k-1}}^{k-1} + bG_1^k\right)/2\right)}{\left(\sum_{n=1}^{N_{k-1}} w_n + t_1^k\right)}. \quad (2)$$

Case 4

Figure 7:
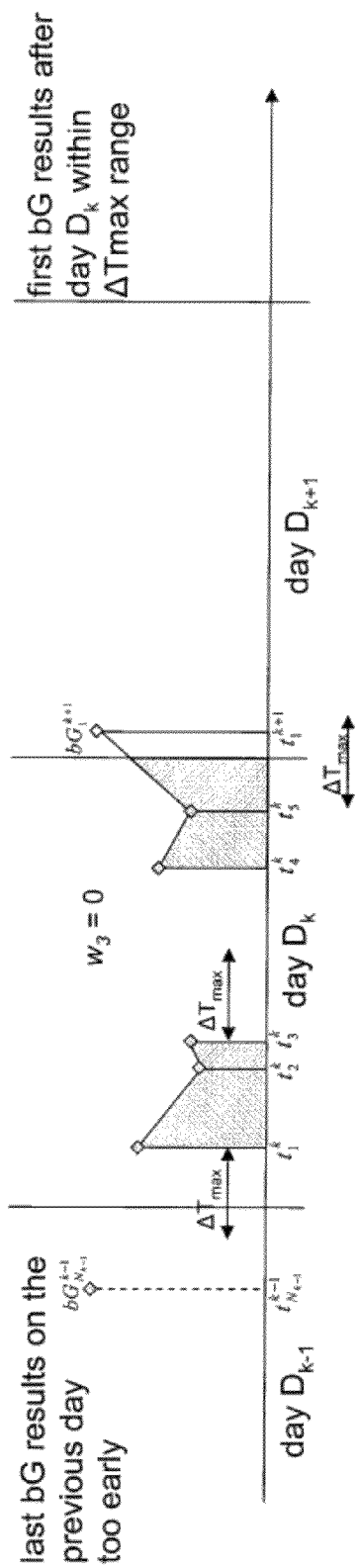
FIG. 7 is graphical representations of calculating daily weighted averages of spot monitoring glucose measurements (or derived quantities) with time-based weights in a fourth use case scenario according to the present invention.

With reference to FIG. 7, as shown the last bG result $bG_{N_{k-1}}^{k-1}$ on the previous day $D_{k-1}$ is too early thereby exceeding the maximum time interval value $\Delta T_{max}$ as well as the interval again between bG results $bG_3^k$ and $bG_4^k$; however, the first bG result $bG_1^{k+1}$ on the day after $D_k$ is within the maximum time interval. Therefore, in such a use case situation, the following logic is employed by the method. If the average daily glucose value will not give a not_a_number result, avg_bG$_k \ne$ NaN, and the given day $D_k$ is the first day that the bG meter 100 has been used to collect glucose measurements or there are no results for the previous day $D_{k-1}$ or the last bG result of the previous day is more than $\Delta T_{max}$ before the first measurement of day $D_k$, and the first measurement $(bG_{1,}^{k+1}t_1^{k+1})$ after day $D_k$ is not more than the value $\Delta T_{max}$ later than the last measurement on day $D_k$, then the average daily glucose value for $D_k$ is calculated according to equation (3) hereafter.

$$\text{avg\_bG}_k = \frac{\left(\text{sum\_bG}_k^* + (1440 - t_{N_k}^k) \cdot \left(bG_{N_k}^k + bG_1^{k+1}\right)/2\right)}{\left(\sum_{n=1}^{N_{k-1}} w_n + 1440 - t_{N_k}^k\right)}. \quad (3)$$

Case 5

Figure 8:
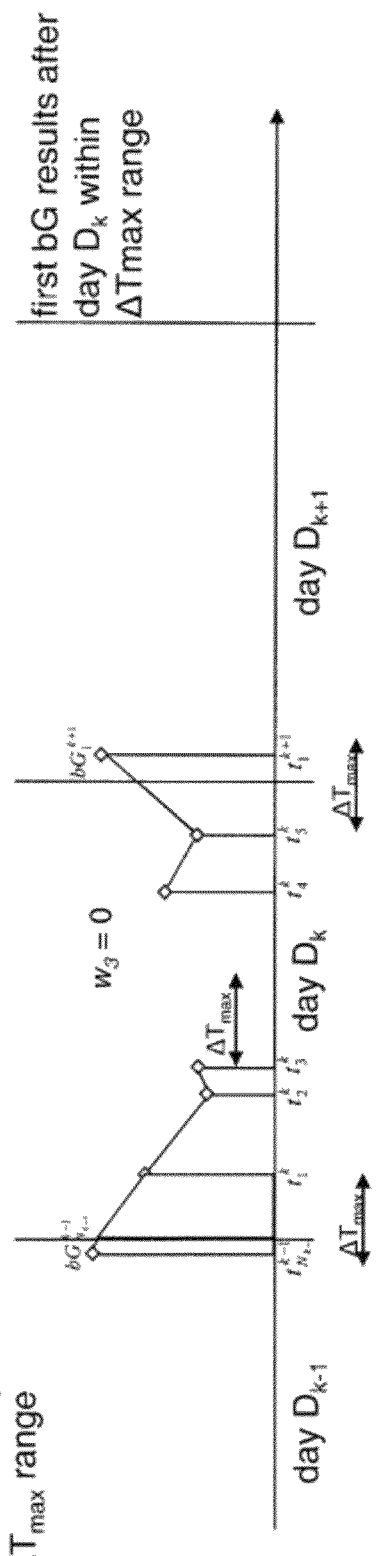
FIG. 8 is graphical representations of calculating daily weighted averages of spot monitoring glucose measurements (or derived quantities) with time-based weights in a fifth use case scenario according to the present invention.

With reference to FIG. 8, as shown the last bG result $bG_{N_{k-1}}^{k-1}$ on the previous clay $D_{k-1}$ and the first bG result $bG_1^{k+1}$ on the day after $D_k$ is with the maximum time interval $\Delta T_{max}$. In this example, the interval again between bG results $bG_3^k$ and $bG_4^k$ exceeds the maximum time interval value. Therefore, in such a use case situation, the following logic is employed by the method. If the average daily glucose value will not give a not_a_number result, avg_bG$_k \ne$ NaN, and the last bG result $(bG_{N_{k-1},}^{k-1}t_{N_{k-1}}^{k-1})$ of the previous day Dk-1 is less than or equal to $\Delta T_{max}$ before the first measurement of day $D_k$) and (the first measurement $(bG_{1,}^{k+1}t_1^{k+1})$ after clay $D_k$ is not more than $\Delta T_{max}$ later than the last measurement on clay $D_k$), then the average daily glucose value for $D_k$ is calculated according to equation (4) hereafter.

$$\text{avg\_bG}_k = \frac{\left(\text{sum\_bG}_k^* + \left(t_1^k \cdot \left(bG_{N_{k-1}}^{k-1} + bG_1^k\right)\right) + (1440 - t_{N_k}^k) \cdot \left(bG_{N_k}^k + bG_1^{k+1}\right)\right)/2}{\left(\sum_{n=1}^{N_{k-1}} w_n + t_1^k + 1440 - t_{N_k}^k\right)}. \quad (4)$$

Using the daily weighted average (with time-based weights) according to the present invention instead of an unweighted algebraic average of the glucose readings over a given day has the advantage to be much less susceptible to multiple measurements taken in case of hypo- or hyperglycemic events. The quantity $\Delta T_{max}$ limits the weight for a given measurement in case the time interval between two consecutive measurements is too long to be acceptable. In this case we accept that we do not know the behavior of the glucose in this interval.

The principle described above can be implemented in various ways. For example, in the above example, using the trapezoidal approximation of the area under the bG curve could be replaced by using an alternative function to interpolate between adjacent bG results and employing a suitable approximation of the integral. However, the necessary effort and logic around case handling become more cumbersome.

The following pseudo code example provided in Table 2 describes one software embodiment which could be implemented on bg meter 100, or provided on removable storage 118, 120, or over network 136. The below pseudo code example provides time weighted averages resulting from a course of calculations associated with measurements having a bG result. Each bG result is assigned a time and date (bG, t, date), and if a previous bG result exists, then the analysis provided by the pseudo code is carried out by the bG meter 100. It is to be appreciated that the term ((t, date)—(t_prev, date_prev)) provided in Table 2 denotes the time difference, for example, in minutes between a first time point t and a second time point t_prev where the two time points belong to different dates i.e., date and date_prev, respectively. The term DeltaTmax is the maximum allowed time between consecutive measurements, and the term W_Dk is a time based weight. The term avg_bG is the daily weighted average. The term sum_Dk is the weighted sum. The term cdate is an index of a do-loop running from previous date +1 to the current date−1. This loop is used to assign NaN to the average glucose for days where no measurement has been provided. This step is used since the average glucose for a given day is calculated when the first measurement after this day has been taken. Finally, the term measurements_today is a counter used to count the number of measurements captured by the bG meter 100 during the given day, date. After computing the daily weighted average over the given day, the value of avg_bG is stored in memory 112.

TABLE 2

Pseudo code example providing time weighted averages retrieve previous result (bG_prev, t_prev, date_prev);
  if date ≠ date_prev then do;
    if sum_Dk ≠ 0 then do;
      if ((t, date) − (t_prev, date_prev)) <= DeltaTmax then do;
        deltaT = 1440 − t_prev;
        W_Dk = W_Dk + deltaT;
        sum_Dk = sum_Dk + deltaT * (bG + bG_prev)/2;
      end;
      avg_bG = sum_Dk / W_Dk;
    else TABLE 2-continued Pseudo code example providing time weighted averages avg_bG = NaN;
    end;
    store (avg_bG, date_prev);
    do cdate = date_prev+1 to date−1;
      avg_bG = NaN;
      store (avg_bG, cdate);
    end;

TABLE 2-continued

Pseudo code example providing time weighted averages

```
    measurements_today = 1;
    if ((t, date) - (t_prev, date_prev)) <= DeltaTmax then do;
        W_Dk = t;
        sum_Dk = t * (bG + bG_prev)/2;
        end;
    else
        sum_Dk = 0;
        W_Dk = 0;
        end;
    end;
  else;
    measurement_today = measurement_today + 1;
    deltaT = t - t_prev;
    if deltaT <= deltaTmax then do;
        sum_Dk = sum_Dk + deltaT * (bG + bg_prev)/2;
        W_Dk = W_Dk + deltaT;
        end;
    end;
  end;
else do;
    sum_Dk = 0;
    W_Dk = 0;
    measurements_today = 1;
    end;
store current result (bG, t, date);
```

In still other embodiments, the bG meter 100 may use the stored daily weighted averages to calculate a long term weighted average with weights that decline exponentially or linearly over time. In addition, the above described weighting scheme is not only useful for bG measurements but can also sensibly applied when calculating derived quantities that can be found in the literature.

The invention is not limited to the embodiments described above. The functionality itself as well as the graphical user interface may be modified in many ways. Particularly, they may be adapted to the computing and display equipment used, especially to its input means, kind of display, display size, computing power, memory size, etc.

The glucose measurements are not restricted to measurements of the glucose (bG) level but may be directed to other glucose levels, such as e.g. glucose levels measured in the interstitial fluid.

In summary, it is to be noted that the invention provides a method as well as an apparatus with a time-based weighting scheme for processing a chronological sequence of measurements of a time dependent physiological parameter measured in or on a human body, and in particular, of a glucose concentration in a body fluid of a patient, that enables the patient to improve his self-management skills concerning his therapy.

What is claimed is:

1. A method for calculating daily weighted averages of glucose measurements collected at a different time with time-based weights comprising:
    receiving, by a computer device, a plurality of glucose measurements for a patient from a glucose meter;
    determining, by the computer device, whether each time interval between two consecutive glucose measurements in the plurality of glucose measurements exceeds a predefined maximum time interval value;
    computing, by the computer device, electronically an average daily glucose value, which represents the daily weighted average of the glucose measurements, using time based weights with the glucose measurements, wherein only consecutive glucose measurements in the plurality of glucose measurements with acceptable time intervals that do not exceed the predefined maximum time interval contribute to the average daily glucose value; and
    reporting, by the computer device, the computed daily weighted average of the glucose measurements, where the steps of determining, computing and reporting are implemented by computer executable instructions executed by a computer processor of the computing device.

2. The method of claim 1, further comprises providing the plurality of glucose measurements each collected at a different time in at least one of a personal digital assistant or a glucose meter.

3. The method of claim 2, wherein the personal digital assistant or the glucose meter is equipped with memory and processing capabilities to process a chronological sequence of measurements of a time dependent parameter measured in or on the human body.

4. A system for calculating daily weighted averages of glucose measurements collected at a different time with time-based weights comprising:
    a processor programmed to:
        receiving a plurality of glucose measurements for a patient;
        determine whether each time interval between two consecutive glucose measurements in the plurality of glucose measurements exceeds a predefined maximum time interval length;
        compute an average daily glucose value, which represents the daily weighted average of the glucose measurements, using time based weights with the glucose measurements, wherein only consecutive glucose measurements in the plurality of glucose measurements with acceptable time intervals that do not exceed the predefined maximum time interval contribute to the average daily glucose value; and
        provide the computed daily weighted average of the glucose measurements.

5. The system of claim 4, wherein the processor is further programmed to receive the plurality of glucose measurements each collected at a different time in at least one of a personal digital assistant or a glucose meter.

6. The system of claim 5, wherein the personal digital assistant or the glucose meter is equipped with memory and processing capabilities to process a chronological sequence of measurements of a time dependent parameter measured in or on the human body.

7. The method of claim 1 further comprises measuring one or more of the plurality of glucose measurements using the computer device.

8. The method of claim 1 further comprises administering insulin to the patient based in part on the computed daily weighted average.

9. The system of claim 4 wherein the processor is integrated into a glucose meter and the glucose measure operates to measure glucose of the patient.

* * * * *